United States Patent
Sorensen et al.

(10) Patent No.: US 7,455,520 B2
(45) Date of Patent: Nov. 25, 2008

(54) DENTAL PRACTICE OPERATING SYSTEM

(75) Inventors: Kim Sorensen, Nærum (DK); Peter Bojsen Sorensen, Charlottenlund (DK)

(73) Assignee: XO Care A/S, Horsholm (DK)

( * ) Notice: Subject to any disclaimer, the term of this patent is extended or adjusted under 35 U.S.C. 154(b) by 29 days.

(21) Appl. No.: 11/493,666

(22) Filed: Jul. 27, 2006

(65) Prior Publication Data

US 2007/0026359 A1 Feb. 1, 2007

Related U.S. Application Data

(63) Continuation of application No. PCT/DK2004/000059, filed on Jan. 27, 2004.

(51) Int. Cl.
*A61C 1/00* (2006.01)
*A61G 15/14* (2006.01)

(52) U.S. Cl. .......................... 433/98; 433/101

(58) Field of Classification Search .................. 433/98, 433/108, 77, 79, 101
See application file for complete search history.

(56) References Cited

U.S. PATENT DOCUMENTS

| | | | |
|---|---|---|---|
| 5,300,926 A | 4/1994 | Stoeckl | |
| 5,422,521 A | 6/1995 | Neer et al. | |
| 5,812,397 A * | 9/1998 | Pech et al. | 700/81 |
| 5,883,615 A | 3/1999 | Fago et al. | |
| 5,931,669 A * | 8/1999 | Fornoff et al. | 433/28 |
| 7,058,998 B2 * | 6/2006 | Diller et al. | 5/614 |
| 2003/0232305 A1 * | 12/2003 | Warner | 433/98 |
| 2005/0130098 A1 * | 6/2005 | Warner | 433/77 |
| 2005/0186533 A1 * | 8/2005 | Cohen | 433/98 |
| 2006/0177795 A1 * | 8/2006 | Sorensen et al. | 433/98 |

FOREIGN PATENT DOCUMENTS

| | | |
|---|---|---|
| EP | 0 391 967 B1 | 8/1992 |
| EP | 0 734 689 A1 | 10/1996 |
| EP | 1 010 404 A2 | 6/2000 |

OTHER PUBLICATIONS

International Preliminary Report on Patentability issued in PCT/DK2004/000059.

* cited by examiner

*Primary Examiner*—Ralph A Lewis
(74) *Attorney, Agent, or Firm*—Buchanan Ingersoll & Rooney PC (57) ABSTRACT

A novel dental practice operation system affords computer controlled activation and control of a multitude of instrument operation and auxiliary functions by providing a plurality of distinct functionalities of at least one activation device for activation and control signals for a dental unit and a patient's rest. Increased efficiency for the dentist or dental team with increased integration of instrument control and auxiliary functions as well as operation of facilities provided by external sources is provided by simultaneous computer displayed guidance to the dentist of a first configuration of individually selectable symbols representing a number of distinct functionalities of the activation device and a second configuration of individually selectable symbols representing functions executable by a distinct functionality of the activation device made available by activation of a selected symbol in said first configuration.

24 Claims, 9 Drawing Sheets

DENTAL PRACTICE OPERATING SYSTEM

This application is a continuation application of International Application No. PCT/DK2004/000059 filed on Jan. 27, 2004 and designating the United States.

FIELD OF THE INVENTION

The present invention relates to a new generation of operating systems for a dental practice.

BACKGROUND DISCUSSION

Computerized control of the operation of dental instruments in a dental unit as well as the performance of various auxiliary functions not related to the instrument operation as such is well known in the art. A typical example in the prior art is disclosed in applicant's European patent EP-B-0 391 967, which discloses a dental unit including a microprocessor for supervision and control of instrument operation as well as a range of auxiliary functions, whereby instruments and auxiliary functions can be selected by means of a display with associated selection means.

A further example of computerized operation of a dental working environment including a dental unit with dental instrument and a patient's chair is disclosed in U.S. Pat. No. 5,300,926, in which a single actuation device in the form of a foot switch, that can be brought from an initial position into working positions, is used for selection and control of a variety of functions, the user being guided by display of function display elements with symbol identifiers and optical signals on a display on a front side of the dental unit.

In a still further example disclosed in EP-A-0 734 689 a system for activating and monitoring a dental unit comprises a main console consisting of a display or viewer including a first display portion defining a fixed number of display fields for operating functions or data or fields for accessing display pages containing accessory function data and a second display portion defining at least part of the display fields for the accessory function data depending on or irrespective of the type of display page, the function data or access fields of the first and second display portions being controlled or activated by first and second control means, respectively, arranged on the main console in positions outside the display or viewer, said control means being typically in the form of push-button configurations and separate from the control or activation device for operational functions of the dental instruments.

On the background of such prior art systems it is an overall object of the invention to provide an automated dental practice operating system to select, control and monitor all functions needed during a dental treatment with significantly increased efficiency for the dentist or the dental team, with increased integration of the control of dental instruments, auxiliary functions and operation of facilities available from source external with respect to the dental work place and with high flexibility in terms of user individual configuration of a variety of elements of the system.

SUMMARY

To achieve this and other objects as will become clear from the following description the invention relates more specifically to a dental practice operating system comprising a dental unit including an instrument holder for a number of dental instruments, which are individually selectable by removal from the holder, and means for control and execution of a plurality of functions related to a dental treatment including operational functions for said dental instruments and a first group of auxiliary functions, an adjustable patient's rest comprising means for control and execution of adjustment functions thereof, at least one multi-function activation device incorporating at least one operating member for independent execution of a number of distinct operational functions for dental instruments as well as auxiliary and/or adjustments functions, and computer means connected with said at least one multi-function activation device and said dental unit and patient's rest and comprising means for changing a functionality of said at least one activation device between a plurality of distinct functionalities, in each of which said at least one operating member is operable for execution of a distinct group of said operational, auxiliary and/or adjustments functions, said computer means including interactive display means for display of a configuration of symbols representing the distinct group of said operational, auxiliary and/or adjustments functions executable by a distinct functionality of said at least one activation device.

According to the invention, the dental practice operating system thus defined is characterized in that said computer means includes a user interface for simultaneous display on said display means of a first configuration of individually selectable symbols representing a number of said plurality of distinct functionalities and a second configuration of individually selectable symbols including, for the distinct functionality represented by a selected symbol in said first configuration, a number of symbols representing operational, auxiliary and/or adjustments functions of the distinct group of functions executable by the distinct functionality represented by said selected symbol, said second configuration of symbols including at least one further symbol representing a change of the functionality of the multi-function activation device, and means for controlling the multi-function activation device for individual execution of an operational, auxiliary and/or adjustment function or change of functionality represented by a symbol of said second configuration including said further symbol.

As a result of the distinct display of the first and second symbol configurations, typically in different sections of a conventional PC display screen, any functionality offered by the activation device for providing a set of activation or control signals for the execution of individual functions of a group of functions may be displayed during the dental treatment in the first configuration of symbols, whereas each actual function, that can be executed by an activation and control signal belonging to a distinct functionality represented by a symbol in the first configuration, will be represented by a symbol in the second configuration to be selectable for actuation by the corresponding activation or control signal from the activation device.

Thereby, an easily understandable guidance for the execution of functions such as instrument operation and adjustment, adjustment of the patient's rest and a variety of auxiliary function is made available to the dentist at any time during a dental treatment.

The multi-function activation device of the operating system may comprise a single activation device or a combination of activation devices. A single activation device may comprise a single operating member operable to provide a number of activation or control signals for individual functions, or it may comprise several operating members to increase the number of executable functions. More than one activation device, each including one or more operating members may also be used. Typical activation devices may include a foot switch, a mouse, a joystick, a keyboard, an interactive touch screen, a speech command device or any other conventional form of computer input device.

In a presently preferred embodiment the multi-function activation device comprises a first operating member and a second operating member, said activation and control signals being provided by individual distinct operation of said operating members. By execution of all functions needed during a dental treatment by means of a single foot operated device the use of manually operated activation device and the risk of cross-contamination during a dental treatment resulting therefrom is avoided.

In an actually preferred embodiment, the symbols of the first configuration are displayed by said display means as individual cells of a single linear bar of cells to facilitate individual selection and activation of the symbols by operation procedures well known to any user familiar with conventional PC operation.

The symbols of the second configuration may in a similar way be displayed in a pictorial representation indicating each distinct operation of each operating member of the activation device. In a preferred embodiment including a foot-operated multi-function activation device the symbols of said second configuration may advantageously be displayed as individual cells overlying a pictorial representation of the multi-function activation device including each operating member thereof with each cell positioned in an unambiguous relationship to the distinct operation of the specific operating member associated with the distinct function represented by the symbol of the cell.

For easy selection and activation of a desired functionality of the activation device or devices each symbol of said first configuration may advantageously be switchable between a non-selected state, a selected stated and an activated state by a distinct activation signal from the activation device, said non-selected, selected an activated states being displayed with distinct visual characteristics by the display means.

In a preferred embodiment using a foot-operated multi-function activation device as mentioned above, in which the first operating member comprises a foot-operated instrument operation member for operation of a selected dental instrument by movement in one and the other of two linearly aligned, but opposite directions and affording a further distinct operation by movement in a direction orthogonal with respect to said linearly aligned directions, a simple and relatively straight procedure for any user familiar with conventional PC operation switching between activation and deactivation of a selected symbol may be executed by said further distinct operation of said foot-operated instrument operation member, whereas selection of a new symbol within the first configuration in the deactivated state only of all symbols therein may be executed by operation of said foot-operated instrument operation member in any of said two linearly aligned directions.

As known per se from convention PC operation the selection of one or more cells in the first configuration may alternatively, in the deactivated state of all cells therein, by made by a distinct short-cut operation that may preferably comprise not more than two distinct operations.

As a further advantageous alternative option to the standard and the conventional short-cut operations direct meta action selection of a desired functionality may be used by including in the first configuration of symbols at least one symbol representing a group of functions divided in at least two sub-groups of functions executable by distinct functionalities of the activation device, distinct symbols representing said sub-groups being included in the second configuration of symbols for switching between said distinct functionalities by direct selection of any of said distinct symbols.

For the operation of functions conventionally used during a dental treatment such as instrument and chair functions and auxiliary functions operable via the dental unit the first configuration of symbols may preferably, by selection of a dental instrument by removal from the instrument holder, be switched to include symbols representing operational functions and/or parameters of the selected instrument, whereas with all instrument resting in the instrument holder the first configuration of symbols will be in a default mode including symbols representing distinct functionalities of said activation device other than instrument operation.

In addition to operation of these functions conventionally used during a dental treatment the invention offers as a significant advantage, however, the possibility of controlling a second group of auxiliary functions provided by an external facility by including in said default mode of the first configuration of symbols at least one symbol representing an additional functionality of the activation devices for controlling such a second group of auxiliary functions related to the dental treatment, but provided by an external utility with respect to said dental unit and patient's rest. Typical auxiliary functions, for which this option add further utility to the operating system may include image processing and digital display of X-ray images and video camera inspection during a dental treatment.

The new generation operation system afforded by the invention may be shared by a number of dentists and for this object at least one distinct functionality of the activation devices may be user-configurable, the first configuration of symbols including in the default mode a symbol for selection of a registered user.

BRIEF DESCRIPTION OF THE DRAWING FIGURES

In the following the invention will be explained in more detail by way of a non-limiting embodiment and with reference to the accompanying schematical drawings, in which.

DETAILED DESCRIPTION

Figure 1:
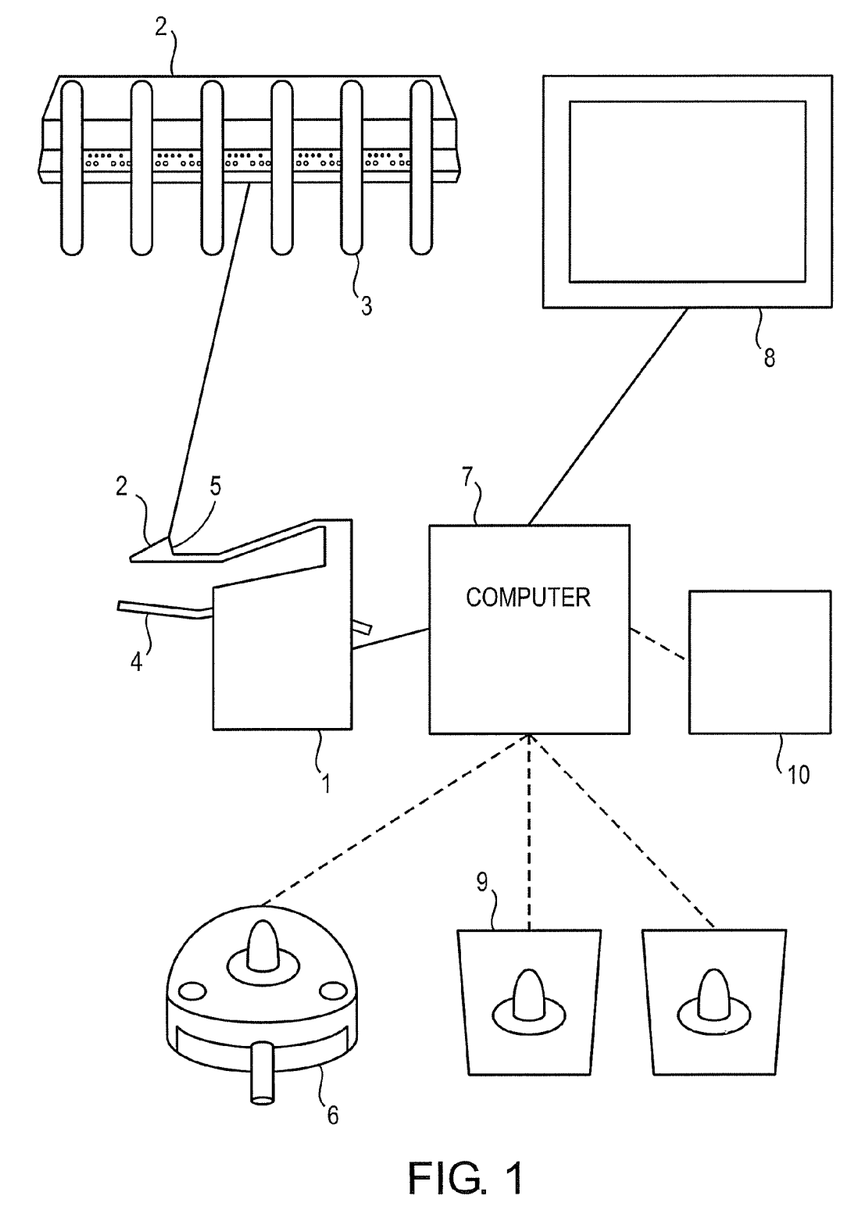
FIG. 1 is a block-schematic diagram showing essential hardware components of a dental practise for use in the operation system of the invention.

The hardware components of a dental practise as illustrated in FIG. 1 comprise a dental unit 1 with an instrument holder 2 providing receptacles for a number of dental instruments 3 that may typically include different types of motor or air-turbine operated instruments. The dental unit 1 is positioned at one side of a patient's rest 4, and the instrument holder 2 is carried by a pivotal or otherwise movable table-like support 5 such that, during a dental treatment the table-like support 5 with the instrument holder 2 may be brought to an operative position overlying the patient's rest 4. For computer controlled operation and parameter control and adjustment of an instrument 3 selected by removal from its receptacle in the instrument holder 2 a foot-operated activation device 6 is provided, which may serve also for the practise operation system according to the invention, the dental unit 1 and the activation device 6 communicate with computer means 7 including a microprocessor and user interface. For visual presentation of the actual state of the dental unit 1 and dental instruments 3 and guidance of the dentist during a dental treatment a display 8 such as a conventional PC screen is connected with the computer means 7.

As illustrated in dashed lines one or more additional activation devices 9 and an external facility 10 for additional auxiliary functions may be connected with the computer means 7 as well.

Figure 2:
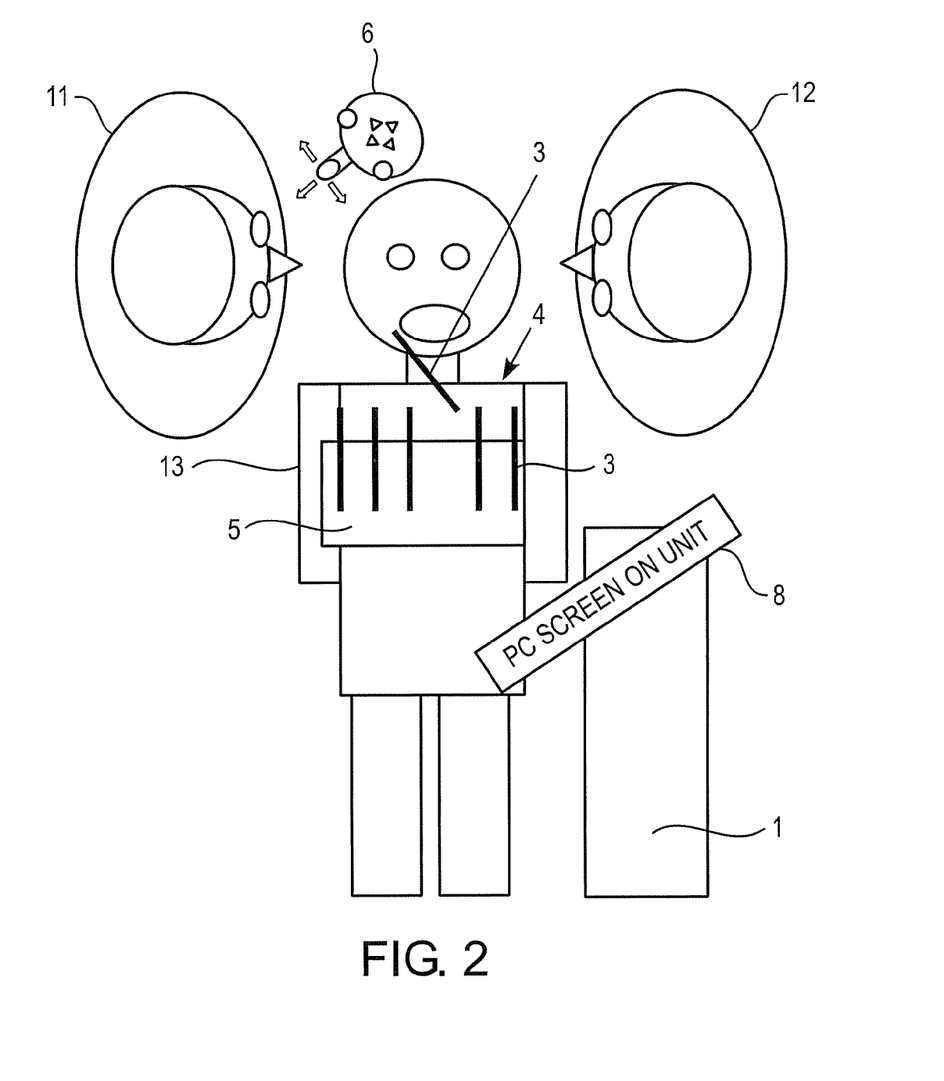
FIG. 2 shows an example of a general arrangement of a dental working environment as viewed from above.

As shown in FIG. 2 the overall arrangement of the dental working environment include working positions 11 and 12 for the dentist and a dental nurse, respectively, disposed at either side of the patient 13 resting on the patient's rest 4 to provide easy access for the dentist and the nurse to the dental instruments 3.

Figure 3:
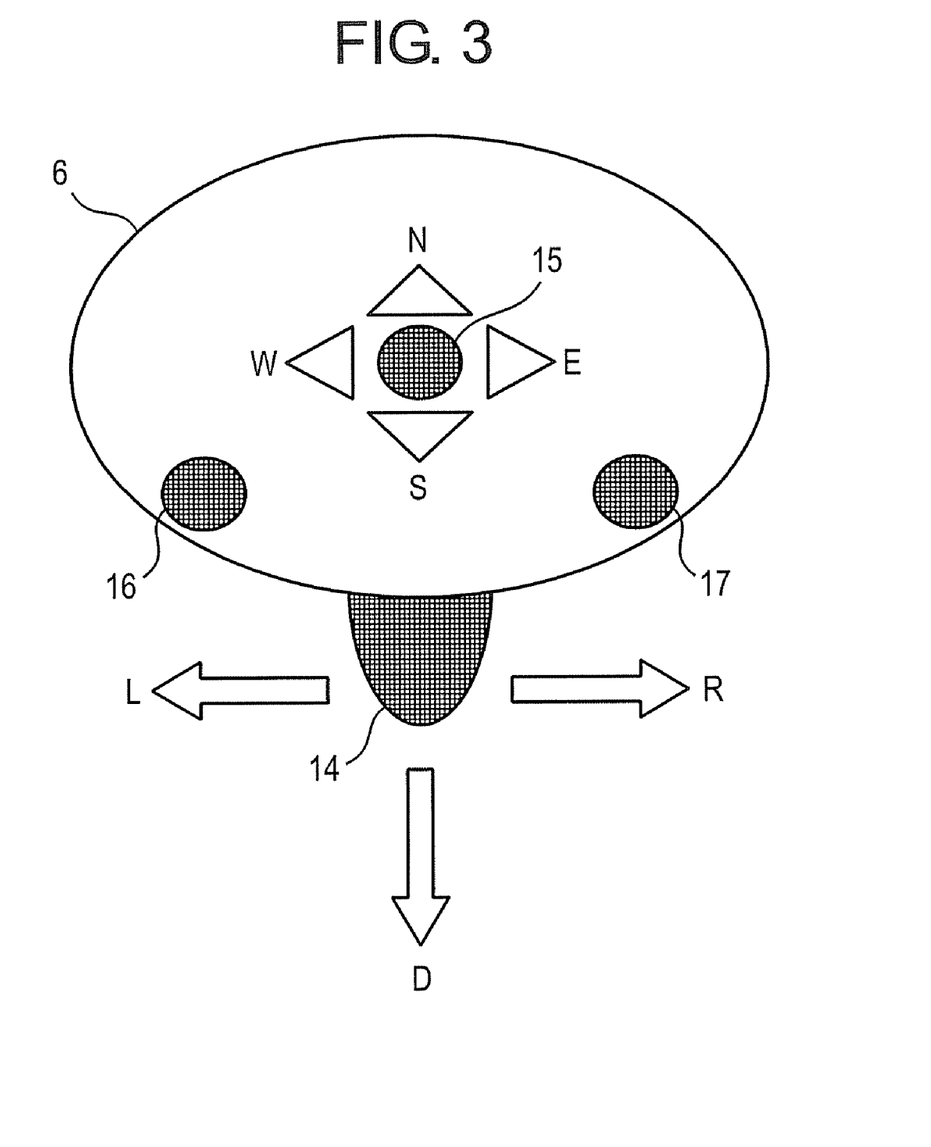
FIG. 3 is a schematical representation of an embodiment of a foot operated multi-function activation device for use in the operating system.

In the illustrated arrangement the activation device 6 is a multi-function foot-switch shown in more detail in FIG. 3 and being disposed on the floor to be easy operable by the dentist, in the illustrated arrangement by us of his left foot.

The display 8 in the form of a conventional PC screen may be disposed of the top and carried by the dental unit 1 to be easily visible from the working position 11 of the dentist.

The actual arrangement illustrated in FIG. 2, which in its general form bas been disclosed in applicant's co-pending international patent application PCT/DK/00164, filed 2003, the disclosure of which is incorporated herein by reference, is only a single example of the possible disposition of a dental working environment, however. Thus, the individual hardware components may be positioned otherwise than illustrated and during certain forms of dental treatment the dentist in the position 11 may work without the assistance of the nurse.

Whereas the foot-operated activation device may in a preferred embodiment be used as s single activation device for the practise operation system of the invention other possible forms of activation devices may be used as well and, in particular, the use of additional activation devices such as an activation device for operation by the dental nurse for certain auxiliary functions may be foreseen, as will appear from the following.

As shown in more detail in FIG. 3 the multi-function foot-operated action device 6 comprises several operating members.

A first operating member comprises a short arm 14 projecting from a generally elliptical housing for use in the normal instrument operation as customary in the art. The operating arm 14 is movable sidewise from a neutral position in opposite directions as illustrated by arrows L and R designating movement to the left and right, respectively. A third direction of movement for the arm 14 may be a downward movement from the neutral position as illustrated by the arrow D.

A second operating member comprises a joystick-like member 15, which like conventional joysticks is moveable in four different orthogonal with respect to each other as illustrated by the arrows designated N, E, S and W.

In the illustrated embodiment the activation device 6 is provided with two additional operating members in the form of relatively simple press-down buttons 16 and 17.

All operating members 14 to 17 of the activation device 6 are spring-controlled in the sense that for any movement the respective operating member will return to its neutral non-operative position, when the action by the dentist's foot is released.

As will appear the multi-function activation device 6 will thus provide the functionality of providing activation and/or control signals for nine different functions by operation of the operating members 14-17 in the directions described.

The structural design described above for the multi-function activation device 6 bas been disclosed in applicant's above-mentioned co-pending international patent application PCT/DK/00164, the disclosure of which is incorporated herein by reference.

In the illustrated and actually preferred embodiment of the practise operation system according to the invention the multi-function foot-operated activation device 6 is used to control not only the operation of any dental instrument 3, that has been selected for use by removal from its respective receptacle in the instrument holder, but also to provide activation or control signals for any other function needed to be performed or executed during a dental treatment. This has the advantage that all functions are controlled by a single foot-operated activation device, there by avoiding any need for finger-operated devices like a keyboard, a mouse or a touch screen and significantly reducing the risk of cross contamination during a dental treatment.

With the development towards an increasing number of auxiliary functions involved in dental treatment procedures, as will become apparent from the following, the execution and control of all such functions by a single multi-function activation device will have as an evitable consequence that it must be possible to switch the activation device between a corresponding number of functionalities, each comprising a number of distinct functions of functions within the overall number of operations made available by operation of the operating member or members of the activation device.

Typical examples of auxiliary functions, which may have to be activated during a dental treatment in addition to the operation of selected dental instruments, would comprise adjustment of the patient's rest between its operative lying position during the treatment and a sitting position needed by the patient to enter or leave the rest or occasionally have access flushing water, adjustment of parameters for a selected dental instrument such as the maximum speed of a drilling instrument, starting a stop watch to monitor the duration of treatment procedure requiring a certain amount of time for completion, observation of an X-ray image relating to the actual treatment video camera inspection of the dental region under treatment etc.

This increasing number of auxiliary functions strengthens the need for the dentist to be kept adequately and precisely informed about the exact status of the hardware components and the actual functionality of the activation device at any point of time during a dental treatment in order to enable any needed action to be performed in time and avoid unintentional activation of other functions, which are undesirable or might harmfully interfere with the actual stage of the treatment.

By the practise operation system of the invention an advanced solution is provided to these problems as will be apparent from following description of one preferred layout of some of the images as shown in FIGS. 4 to 9, which may be displayed to the dentist on the screen 8 during a dental treatment.

Figure 4:
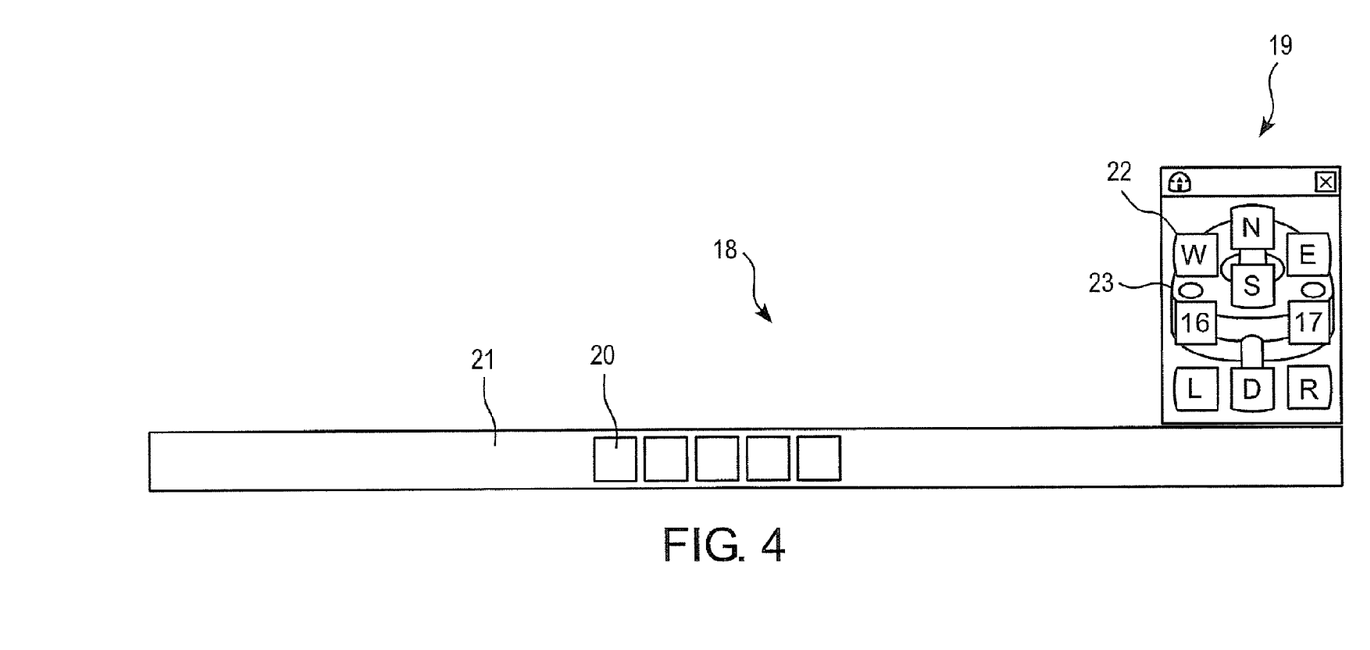
FIG. 4 is a graphic representation of an example of a general layout of the visual display of symbols representing functionalities of an activation device as shown in FIG. 3 and distinct activation and control actions to be executed by such a functionality, respectively.

In FIG. 4 the general image layout controlled by the user interface of the computer 7 comprises in accordance with the invention the simultaneous display of a first configuration 18 of symbols, which each represent one distinct functionality of the activation device or devices, in the illustrated example the multi-function foot-operator 6 shown in FIGS. 1 to 3, and a second configuration 19 of symbols including symbols representing individual distinct functions belonging to a single distinct functionality of the activation device as represented by one of the symbols in the first configuration 18 together with at least one symbol for selection of a symbol within the first configuration 18 to change the activation to another distinct functionality comprising a new set or group of functions.

As shown in FIG. 4 the symbols of the first configuration 18 may advantageously be displayed in the form of individual cells 20 disposed along a single linear bar 21, which may as shown extend in the horizontal direction close to the bottom of the screen, but could obviously also have a vertical orientation and be shifted to a position close to the top of the screen.

To provide clear and unambiguous information about the functions that can be activated or controlled by any distinct functionality of the activation device the symbols of the second configuration 19 is advantageously displayed in a pictorial representation indicating each distinct operation of each operating member of the activation device or devices belonging to the same distinct functionality thereof. For the illustrated preferred embodiment including the multi-function foot-operator 6 this is preferably accomplished by displaying the symbols of the second configuration 19 as individual cells 22 overlying a pictorial representation 23 of the multi-function foot-operator 6 with its operating members 14 to 17, each of the cells 22 being positioned in an unambiguous relationship to the corresponding distinct operation of the specific operation member. This allocation of the cells 22 to the distinct operation of the operating members 14 to 17 is illustrated in FIG. 4 by references corresponding to each specific direction of the movement of the first and second operating members 14 and 15, i.e. L, R, D, N, E, S and W and the reference numerals 16 and 17 for the two press-buttons.

Figure 5:
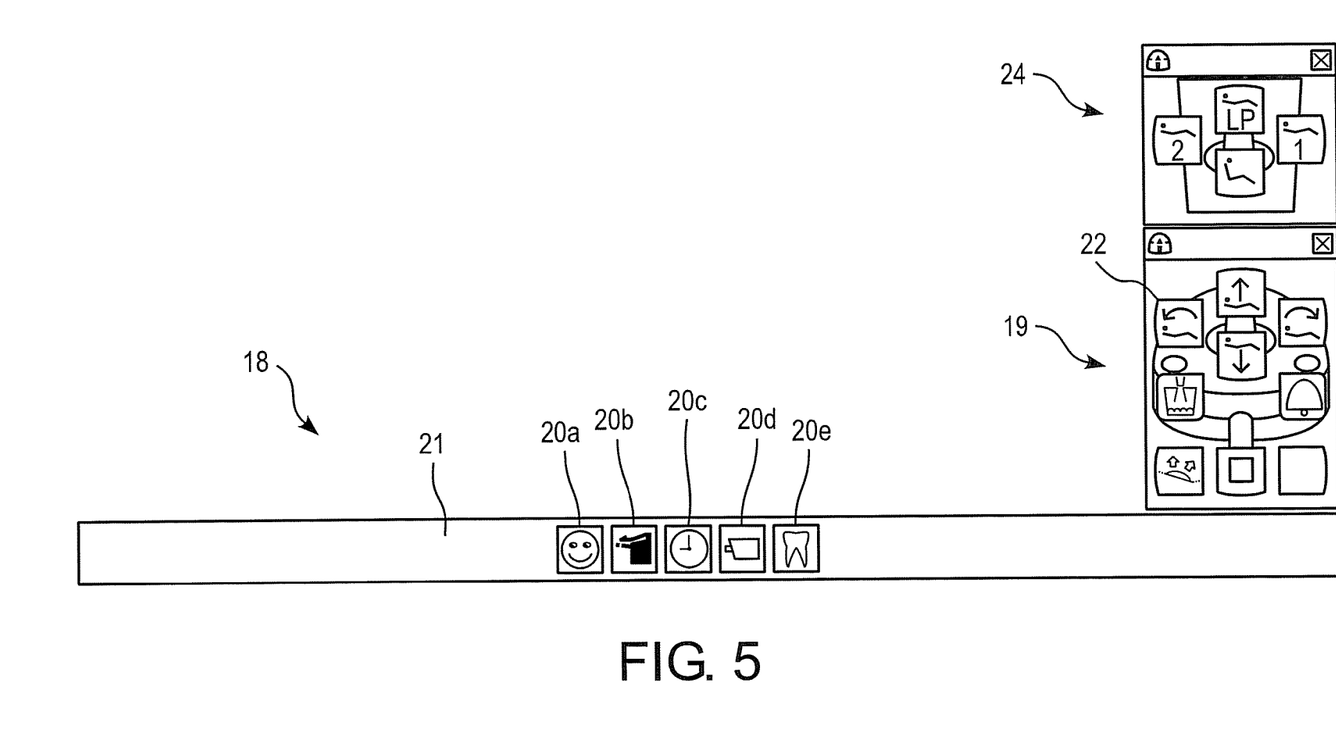
FIGS. 5 to 9 show non-exhaustive examples of the application of the general layout shown in FIG. 4 for activation and control of a variety of functions related to a dental treatment.

In FIG. 5 an example is shown of a default menu shown on the display 8 of a multi-user operation system for use by any of a number of users registered in the computer 7, i.e. the menu displayed when turning on the operation system.

The first symbol configuration 18 comprises five symbols in cells labelled 20 *a, b, c, d,* and *e* each representing an individual distinct functionality. The functions, which can be activated or controlled in this mode, will typically be auxiliary functions relating to adjustment of the patient's rest 4 and to functions, that although not related to operation of the dental instruments 3 are activated via the dental unit 1. The five functionalities represented by cells 20 *a-e* are displayed by graphic symbols as follows:

20*a*: User identification allowing the actual registered user to enter his name and thereby activate his individual configuration of certain user configurable functionalities of the system;
  20*b*: Activation and control of auxiliary functions relating to adjustment of the patient's rest 4 and auxiliary functions operated via the dental unit 1, e.g. filling the patient's water cup or calling the dental nurse;
  20*c*: Activation of a stop watch and timer program allowing start and stop of a stop watch and a number of different timer controlled sound alarm functions;
  20*d*: Activation and control of an external intraoral video camera;
  20*e*: User control of an external digital image processing programme such as the image processing software "Digora" ® available from the Finnish company Soredex for manipulation and display of a digital X-ray image on the screen 8;

As a preferred feature of the invention each of the cells 20 *a-e* of in the horizontal bar 21 representing the first symbol configuration 18 may switchable between a non-selected state, a selected state for preparing the cell for activation and an activated state. In the illustrated example the cell 20*b* representing the functionality of the foot-operator 6 for activation and control of auxiliary functions for the patient's rest and the dental unit.

Accordingly, of the nine different functions illustrated by graphic symbols in the cells 22 of the second configuration 19 the two functions activated by operation of the press-down buttons 16 and 17 are the auxiliary functions operated via the dental unit as exemplified above, whereas as the four functions activated by operation of the second operating member 15 in the directions N, E, S and W comprises raising and lowering of the patients rest adjustment of the back rest thereof. By operation of the first operating member 14 in the direction L inflation of an air cushion in the patient's rest may be activated.

As an important feature, one of the symbols of the second configuration 19, in the illustrated example operation of the first operating member 14 in the downward direction D, is used for switching a selected cell in the first configuration between a selected, but deactivated state and an activated state as shown for the cell 20*b*. In a manner known in the art the display of cells 20 in the first configuration is controlled to provide a clear visual distinction between the non-selected, selected and activated states, for the activated state e.g. by changing the background colour of the cell.

Selection of a new cell 20 in the first configuration 18 may be made only by deactivation of the previously activated cell. The deactivation caused by operation of the operating member 14 in direction D changes the content of the cells in the second configuration 19 e.g. by reserving two cells, e.g. those representing movement of the operating member 14 in the L and R directions for cycling through all the cells of the first configuration by shifting the cell selection to the left or right, respectively, to be described in the following with reference to the example shown in FIG. 6.

The display illustrated in FIG. 5 shows a further advantageous feature by addition of a third configuration 24 of symbols for functions, in this example for adjustment of the patient's rest, which can be activated or controlled by an additional activation device 9 as shown in FIG. 1. The additional activation device may typically be a further foot-operated joystick, e.g. for operation by the dental nurse, affording activation of four functions by operation in the N, E, S and W directions, respectively as for the operating member 15 of the multi-function foot-controller 6.

Figure 6:
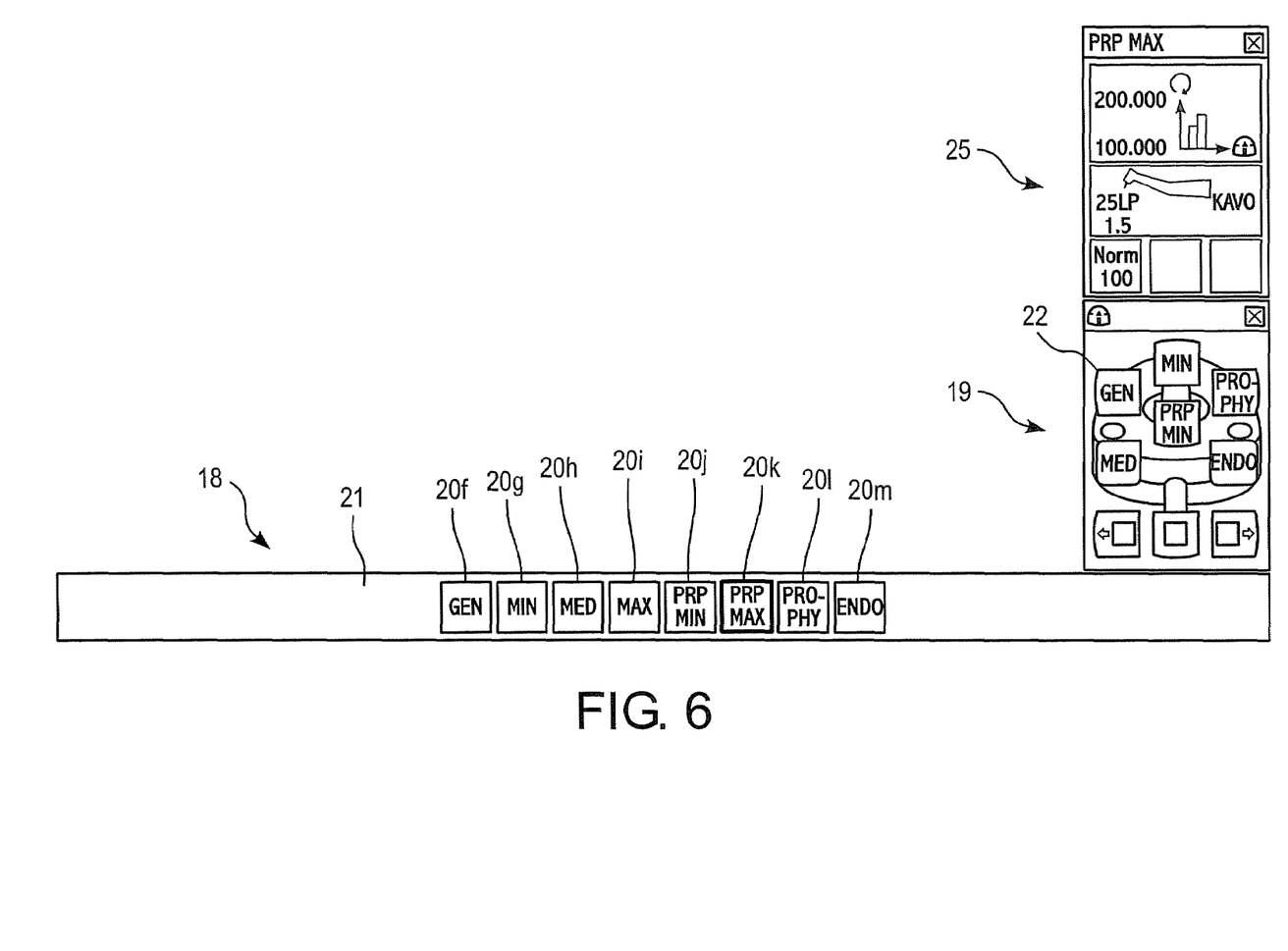
Figure 7:
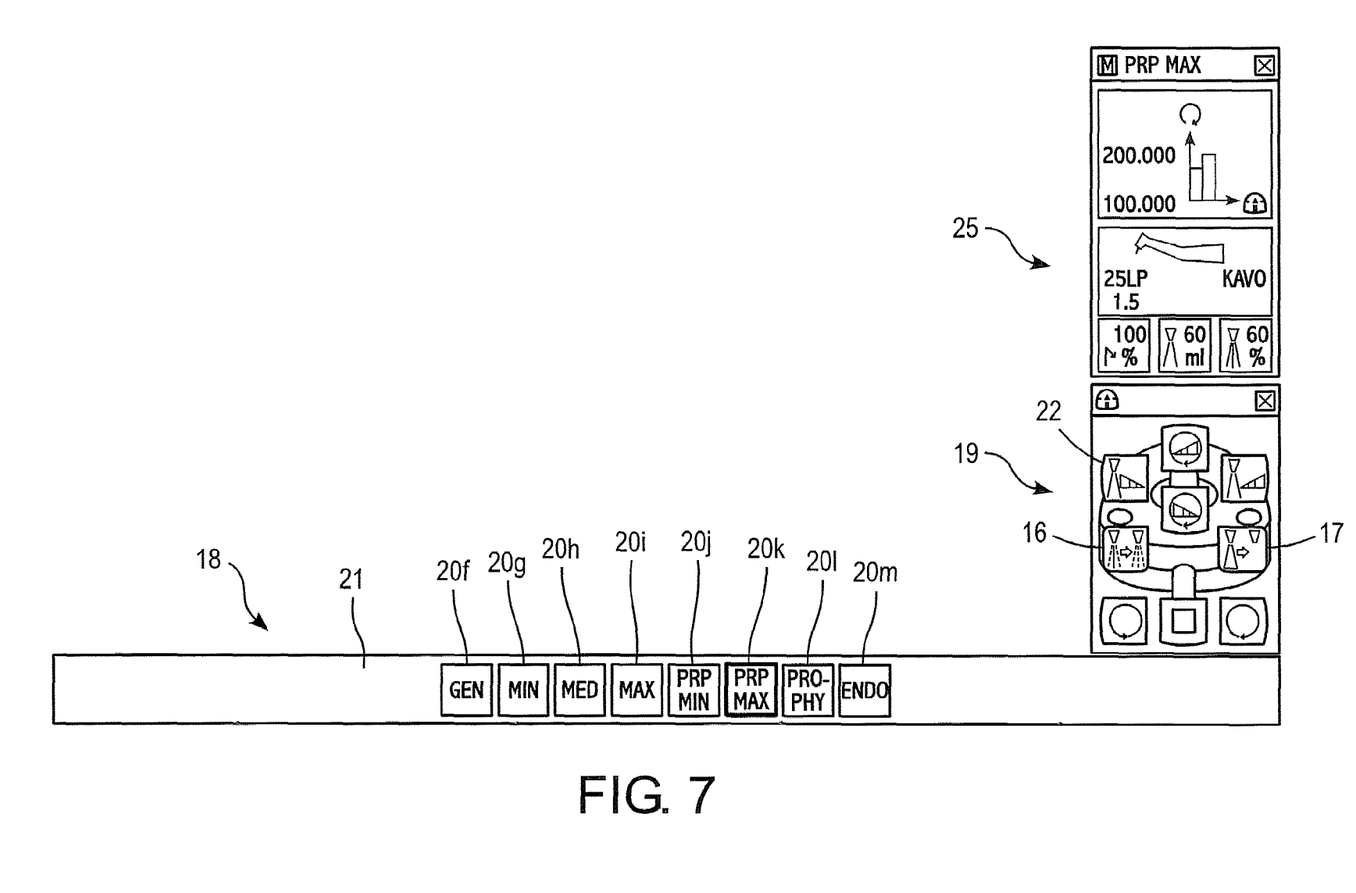

The screen picture examples shown in FIGS. 6 and 7 relate to the operation of a dental instrument, which in the actual presentation is an electric motor driven instrument. By removal of the instrument 3 from its receptacle in the instrument holder 2 the picture shown in FIG. 7 is displayed, in which the first symbol configuration 18 in the illustrated example includes eight symbols indicated abbreviated text denotations such as GEN, MIN, MED, MAX, PRP MIN, PRP MAX, PROFY AND, ENDO contained in cells 20 *f-m*, respectively in the linear horizontal bar 21. The functionalities of the multi-function activation device selectable from the first symbol configuration may for this example briefly be described as follows:

GEN: a general motor program covering the entire speed range, e.g. from 50 to 40,000 rpm, of the selected instrument, with exponential speed control;
  MIN: Operation at low speed, e.g. 50 to 1,000 rpm, with linear control;

MED: Medium-speed operation, e.g. from 1,000 to 20,000 rpm, with linear control;

MAX: High-speed operation, e.g. from 20,000 to 40,000 rpm, with two step control;

PRP MIN: Slow-speed operation for preparation of a tooth;

PRP MAX: High-speed operation in connection with preparation;

PROPHY: Low-speed operation without coolant for polishing of tooth coatings;

ENDO: Low-speed operation without coolant for endodontic treatment:

In the display illustrated in FIG. 6 none of the cells 20 *f-m* in the bar 21 has yet been activated, but the cell 20 *k* for the functionality denoted PRP MIN has been selected for activation. In this mode the symbols in cells D, L and R included in the second configuration 19 is used for activation of a selected cell such as the cell 20*k* and for selection of a new cell by stepping through the cells from the previously selected cell in the left or right direction, respectively, by operation of the first operating member 14 of the multi-function foot-operator 6 in the respective direction, as described in the foregoing.

In the display example in FIG. 6 also the additional feature of selection of a number of the functionalities represented by symbols in the first configuration 18 by a short-cut action is illustrated. By way of example such a short-cut action may be implemented by using the remaining six symbols in the cells 22 of the second configuration 19 for direct selection of any of a corresponding number of the symbols of the first configuration 18 by operation of the joystick-like operating member 15 or the two press-down buttons 16 and 17, i.e. without any need for stepping through the first configuration 18.

Further illustrated in FIG. 6 is an inactive instrument program window 25, generated by the selection of the cell 20*k*.

In the display illustrated in FIG. 7 the selected cell 20*k* denoted PRP MIN has been activated by operation of the first operating member 14 in direction D with the result that the content of symbols in the second configuration is changed to indicate the functionality of the foot-operator 6 now made available for operation. In the illustrated example activation of the symbols representing operation of the first operating member 14 in the L and R directions will cause operation of the selected instrument in either of the two possible directions of rotation, clockwise and counter-clockwise, respectively. The symbols representing operation of the second operation member 15 in the N and S directions may be activated for upward or downward adjustment, respectively, of the maximum speed of the instrument, a graphic illustration of which is presented in the upper section of the instrument program window 25. The symbols of the second configuration 19 representing operation of the second operation member 15 in the E and W directions may be correspondingly be activated for upward or downward adjustment, respectively, of the water content in the coolant spray employed by use of the selected electric motor driven instrument, an indication of this option is provided in the lower section of the instrument program window 25. The symbols of the second configuration 19 representing operation of the press-down buttons 16 and 17 of the foot-operator 6 may be used for changing the combination of water and air cooling to a drilling instrument and enable/disable automatic chip blow, respectively.

In the illustrated example in FIG. 7 a middle section of the instrument program window 25 is used for visual presentation of a specific contra angle for the selected drilling instrument recommended for the speed adjustment displayed in the upper section of the window.

Figure 8:
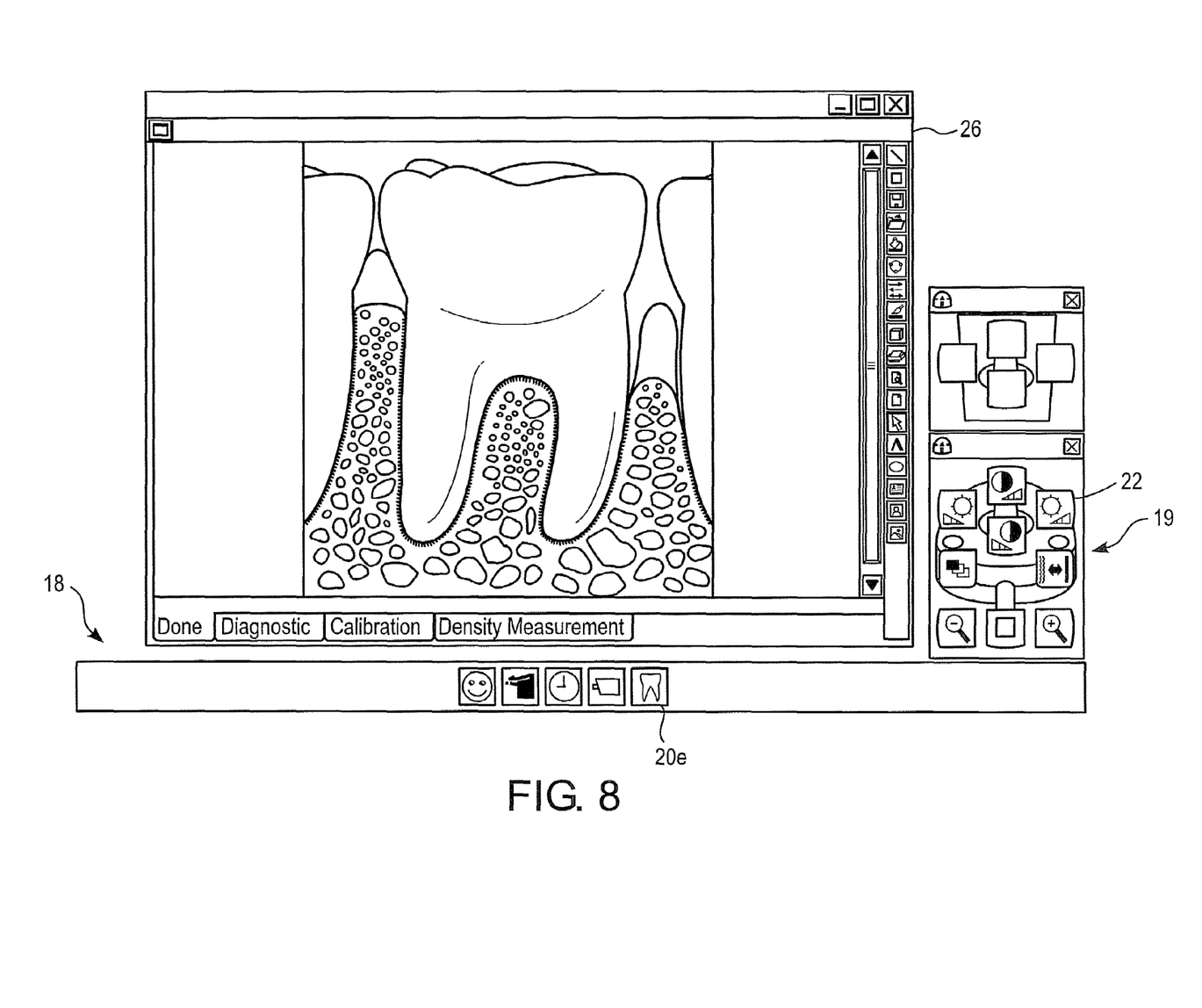

A further advantageous application of the operating system for monitoring and controlling software provided by an external utility is shown in FIG. 8 illustrating as an example activation and control of an image processing program such as the programme "Digura"® mentioned in the foregoing. This functionality of the activation device or devices such as the foot-operator 6 may be selected in the default mode, in which the first symbol configuration 18 will be the same as shown in FIG. 5. By selection of the cell 20*e* of the first configuration 18 and operation of the first operating member 14 in the direction D the image processing programme will become active and a second group of auxiliary function represented by symbols of the second configuration 19 will comprise a number of image processing manipulations that can be activated by operation of the operating members 14 to 17 of the foot-operator 6 for activation of any the cells 22 other than the cell used for activation and deactivation of a selected cell in the first symbol configuration 18.

By activation of the image processing facility a main menu thereof will be displayed in a relative large window 26 and make it possible to retrieve any of a number of digital X-ray images stored by the image processing facility or in the computer 7.

As will appear from FIG. 8 the options made available for activation by a symbol included in the second configuration 19 may include typical image processing procedures like up/down adjustment of brightness and contrast, zoom-in and zoom-out, image retrieval and filtering a retrieved X-ray image in the window 26. By way of the latter option the window 26 displaying the selected image will remain on the computer screen 8, if the functionality represented by the symbols of the first configuration is changed, e.g. by selection of a dental instrument for performing a dental procedure on the tooth shown in the selected image.

When an external facility such as the illustrated image-processing programme provides for individual user configuration of functions included in the second of auxiliary functions the configuration preferred by a registered user is stored by the computer 7 and made available for the user when activating the external facility.

Figure 9:
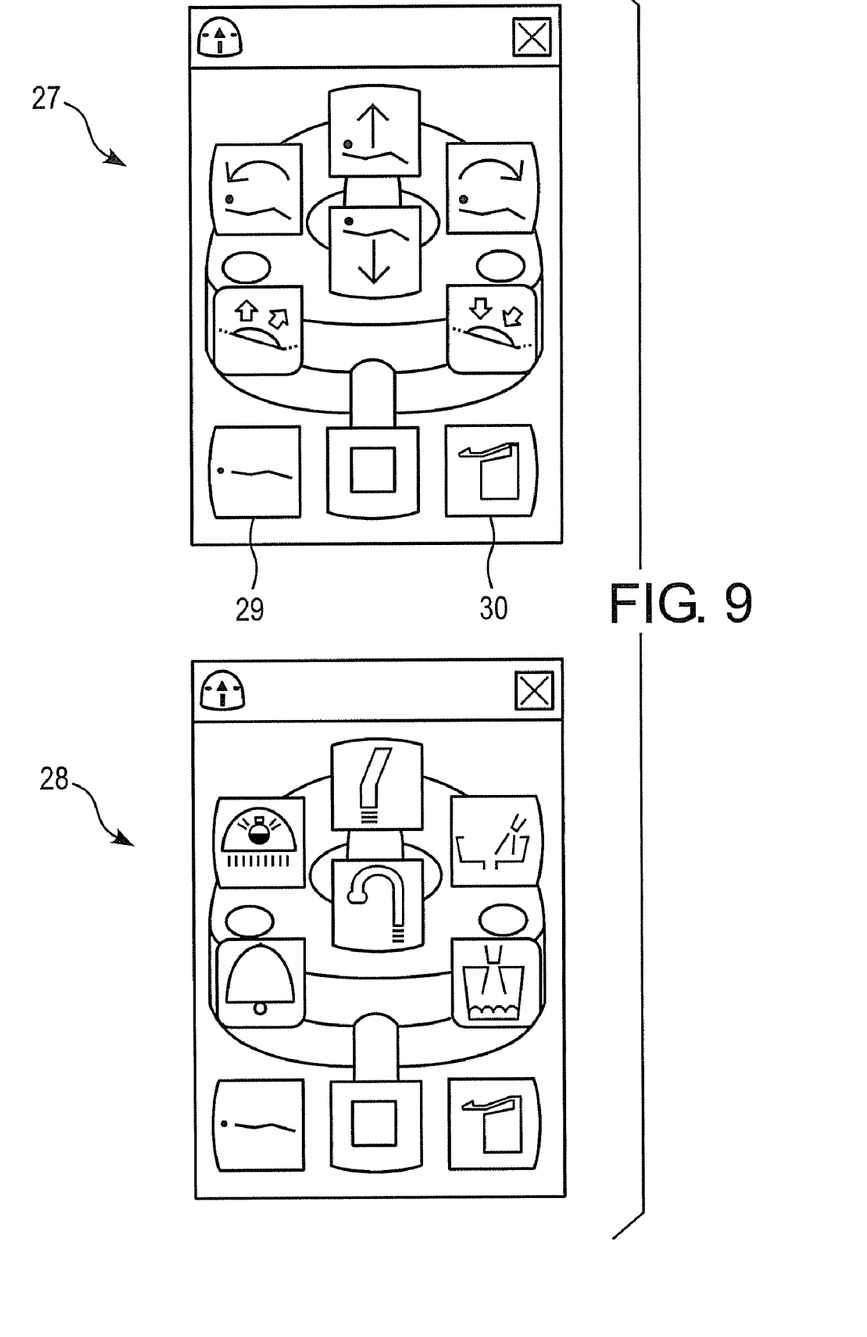

For a group of functions comprising a number of distinct functions exceeding the maximum number of symbols made available for activation by the second symbol configuration 19 a further advantageous short-cut operation possibility is illustrated in FIG. 9.

The group of functions, exemplified by adjustment functions for the patient's rest 4 and auxiliary functions activated via the dental unit 1, may be divided into two or more groups, e.g. e.g. as illustrated two groups for the patient's rest 4 and the dental unit 1, respectively and the second symbol configuration 19, which would otherwise be as illustrated in FIG. 5, may be split into two or more individually selectable sub-configurations, in the illustrated example two sub-groups 27 and 28 containing symbols for the patient's rest adjustment and for activation of auxiliary functions respectively, each of these sub-configurations including symbols for activation of either of the sub-configurations.

By activation of the symbol for the patient's rest/dental unit functions shown in cell 20*b* of the default mode display in FIG. 5 only on of the two sub-configurations 27 and 28 of the illustrated example will be displayed instead of the single second symbol configuration 19 shown in FIG. 5 to allow activation of any of the functions included in the corresponding sub-group. In addition to the symbols representing these functions each of the sub-configurations in the illustrated example 27 and 28 includes two symbols allowing direct Meta action switching between the two sub-configurations 27 and 28 by operation of the first operating member 14 in the L and R directions, in addition to the symbol for activation/ deactivation of the selected symbol in cell 20b of the first configuration 18 by operation of the operating member 14 in the D direction as indicated by 29 and 30, respectively.

Whereas the dental practise operation system according to the invention has been described in the foregoing by way of a number of illustrative examples of groups of distinct that may be included in specific distinct functionalities of the activation device or devices other functions needed or desirable in the operation of a dental practice may be foreseen for integration with the practise operation system without departing from the scope of the invention. Such functions could include for example operation of treatments protocols as disclosed as disclosed in the applicants above-mentioned co-pending international patent application PCT/DK03/00164 as well as control of external dental patient information and/or patient entertainment programs.

The invention claimed is:

1. An operating system for a dental practice, comprising
a dental unit including an instrument holder for a number of dental instruments, which are individually selectable by removal from the holder, and means for control and execution of a plurality of functions related to a dental treatment including operational functions for said dental instruments and a first group of auxiliary functions,
an adjustable patient's rest comprising means for control and execution of adjustment functions thereof,
at least one multi-function activation device incorporating at least one operating member for independent execution of a number of distinct operational function for dental instruments as well as auxiliary and/or adjustments functions, and
computer means connected with said at least one multi-function activation device and said dental unit and patient's rest and comprising means for changing a functionality of said at least one activation device between a plurality of distinct functionalities for execution of distinct groups of said operational, auxiliary and/or adjustments functions, said computer means including interactive display means for display of a configuration of symbols representing the distinct group of said operational, auxiliary and/or adjustments functions executable by a distinct functionality of said at least one activation device,
said computer means further including
a user interface for simultaneous display on said display means of a first configuration of individually selectable symbols representing a number of said plurality of distinct functionalities and a second configuration of individually selectable symbols representing operational, auxiliary and/or adjustments functions of the distinct group of functions executable by the distinct functionality represented by a selected symbol of said first configuration, said second configuration of symbols including at least one further symbol representing a change of the functionality of the at least one activation device, and
means for controlling the multi-function activation device for individual execution of an operational, auxiliary and/or adjustment function or a change of functionality represented by a symbol of said second configuration including said further symbol.

2. A dental practice operating system as claimed in claim 1, wherein said multi-function activation device comprises a first operating member and a second operating member, activation and control signals for said dental unit and said patient's rest being provided by individual distinct operation of said operating members.

3. A dental practice operating system as claimed in claim 2, wherein said first operating member comprises a foot-operated instrument operation member for operation of a selected dental instrument by movement in one and the other of two linearly aligned, but opposite directions and affording a further distinct operation by movement in a direction orthogonal with respect to said linearly aligned directions.

4. A dental practice operating system as claimed in claim 2, wherein said second operating member comprises a foot-operated joystick-like member affording four distinct operations by movement in four orthogonal directions.

5. A dental practice operating system as claimed in claim 2, wherein the multi-function activation device comprises at least one additional foot-operated operating member associated with a single distinct symbol of said second configuration.

6. A dental practice operating system as claimed in claim 2, wherein the symbols of said second configuration are displayed as individual cells overlying a pictorial representation of the multi-function activation device including each operating member thereof with each cell positioned in an unambiguous relationship to the distinct operation of the specific operating member associated with the distinct function represented by the symbol of the cell.

7. A dental practice operating system as claimed in claim 2, wherein an additional activation device is provided and that the simultaneous display by the user interface of said computer means comprises a third configuration of symbols including symbols rep-resenting a sub-group including functions other than those included in the group of functions executable by symbols said second configuration.

8. A dental practice operating system as claimed in claim 1, wherein the symbols of said first configuration are displayed by said display means as individual cells of a single linear bar of cells.

9. A dental practice operating system as claimed in claim 1, wherein the symbols of said second configuration are displayed in a pictorial representation indicating each distinct operation of each operating member of the activation device.

10. A dental practice operating system as claimed in claim 1, wherein each symbol of said first configuration is switchable between a non-selected state, a selected stated and an activated state by a distinct activation signal from the activation device, said non-selected, selected an activated states being displayed with distinct visual characteristics by said display means.

11. A dental practice operating system as claimed in claim 10, wherein said first operating member comprises a foot-operated instrument operation member for operation of a selected dental instrument by movement in one and the other of two linearly aligned, but opposite directions and affording a further distinct operation by movement in a direction orthogonal with respect to said linearly aligned directions, switching of a selected symbol in said first configuration between said activated state and a deactivated state being executed by said further distinct operation of said foot-operated instrument operation member, whereas selection of a new symbol within the first configuration is executable only in the deactivated state of all symbols therein by operation of said foot-operated instrument operation member in any of said two linearly aligned directions.

12. A dental practice operating system as claimed in claim 10, wherein said first operating member comprises a foot-operated instrument operation member for operation of a selected dental instrument by movement in one and the other of two linearly aligned, but opposite directions and affording a further distinct operation by movement in a direction orthogonal with respect to said linearly aligned directions, whereby in the deactivated state of all cells in said first configuration one or more cells thereof is selectable by distinct short-cut operation.

13. A dental practice operating system as claimed in claim 12, wherein said distinct short-cut operation comprises not more than two consecutive distinct operations.

14. A dental practice operating system as claimed in claim 10, wherein said first configuration of symbols includes at least one symbol representing a group of functions comprising a number of sub-groups of functions executable by distinct functionalities of the activation device, said distinct functionalities being displayed in individually selectable sub-configurations of said second configuration, each of said sub-configurations including distinct symbols representing each of said sub-groups for meta-action switching between said distinct functionalities by direct selection of any of said distinct symbols.

15. A dental practice operating system as claimed in claim 14, wherein said sub-groups include said first group of auxiliary functions and said adjustment functions for the patient's rest, respectively.

16. A dental practice operating system as claimed in claim 1, wherein at least one distinct functionality of said activation device is user configurable.

17. A dental practice operating system as claimed in claim 1, wherein by selection of a dental instrument by removal from the instrument holder the first con-figuration of symbols is switched to include symbols representing operational functions and/or parameters of the selected instrument, whereas with all instruments resting in the instrument holder the first configuration of symbols is in a de-fault mode including symbols representing distinct functionalities of said activation device other than instrument operation.

18. A dental practice operating system as claimed in claim 17, wherein each symbol of said first configuration is switchable between a non-selected state, a selected stated and an activated state by a distinct activation signal from the activation device, said non-selected, selected an activated states being displayed with distinct visual characteristics by said display means and by switching of a symbol in said first configuration representing an operational parameter of a selected instrument to said activated state an additional visual presentation of said parameter is displayed by the user interface of said computer means, that the second configuration of symbols including symbols for adjustment of said parameter.

19. A dental practice operating system as claimed in claim 18, wherein in said default mode the first configuration of symbols includes at least one symbol representing an additional functionality of the activation devices for controlling a second group of auxiliary functions related to the dental treatment, but provided by an external utility with respect to said dental unit (1) and patient's rest.

20. A dental practice operating system as claimed in claim 19, wherein said external utility provides for user configuration of one or more auxiliary functions of said second group, said computer means being adapted for storing said user configuration for execution of said one or more auxiliary functions by said additional functionality of the activation device.

21. A dental practice operating system as claimed in claim 17, wherein in said default mode the first configuration of symbols includes at least one symbol representing an additional functionality of the activation devices for controlling a second group of auxiliary functions related to the dental treatment, but provided by an external utility with respect to said dental unit and patient's rest.

22. A dental practice operating system as claimed in claim 21, wherein said external utility provides for user configuration of one or more auxiliary functions of said second group, said computer means being adapted for storing said user configuration for execution of said one or more auxiliary functions by said additional functionality of the activation device.

23. A dental practice operating system as claimed in claim 17, designed as a multi-user system for a number of users registered in said computer means, wherein the first configuration of symbols including in said default mode a symbol for selection of one of said registered users.

24. An operating system for a dental practice, comprising
a dental unit including an instrument holder for a number of dental instruments, which are individually selectable by removal from the holder, a control unit for control and execution of a plurality of functions related to a dental treatment including operational functions for said dental instruments and a first group of auxiliary functions,
an adjustable patient's rest comprising an adjustment unit for control and execution of adjustment functions thereof,
at least one multi-function activation device incorporating at least one operating member, and
a computer connected with said at least one multi-function activation device and said dental unit and said patient's rest and comprising means for selectively changing a functionality of said at least one activation device between a plurality of distinct functionalities, each distinct functionality comprising a distinct group of said operational, auxiliary or adjustment functions which are individually executable by said at least one operating member of said at least one activation device, said computer including an interactive display for display of a configuration of symbols representing the distinct group of said individually executable operational, auxiliary or adjustment functions of the selected distinct functionality,
said computer further including
a user interface for simultaneous display on said display of a first configuration of individually selectable symbols representing a number of said plurality of distinct functionalities, the selected symbol of the first configuration representing the selected distinct functionality, and a second configuration of individually selectable symbols representing the individually executable operational, auxiliary or adjustment functions of the selected distinct functionality, said second configuration of individually selectable symbols including at least one further symbol representing a change of the functionality of the at least one activation device, and
means for controlling the multi-function activation device for individual execution of an operational, auxiliary or adjustment function or a change of the functionality of the at least one activation device represented by a symbol of said second configuration including said further symbol.

* * * * *